(12) United States Patent
Miefalk

(10) Patent No.: US 6,479,017 B2
(45) Date of Patent: Nov. 12, 2002

(54) DEVICE FOR MEASURING AN ELECTRICAL PARAMETER IN THE MILK

(75) Inventor: Håkan Miefalk, Järfälla (SE)

(73) Assignee: DeLaval International AB ( * ) Notice: Subject to any disclaimer, the term of this patent is extended or adjusted under 35 U.S.C. 154(b) by 70 days.

(21) Appl. No.: 09/171,720

(22) PCT Filed: Apr. 21, 1997

(86) PCT No.: PCT/SE97/00671

§ 371 (c)(1),
(2), (4) Date: Mar. 29, 1999

(87) PCT Pub. No.: WO97/40374

PCT Pub. Date: Oct. 30, 1997

(65) Prior Publication Data

US 2001/0039055 A1 Nov. 8, 2001

(30) Foreign Application Priority Data

Apr. 24, 1996 (SE) .............................................. 9601565

(51) Int. Cl.[7] .............................................. A01J 5/013
(52) U.S. Cl. ........................ 422/74; 422/82.01; 436/23; 436/150; 119/14.01; 119/14.14; 119/14.17
(58) Field of Search ................................ 436/149, 150, 436/23; 119/14.01, 14.08, 14.14, 14.17; 422/74, 76, 82.01

(56) References Cited

U.S. PATENT DOCUMENTS 4,112,758 A * 9/1978 Heidecker .................... 73/218
4,325,028 A 4/1982 Takahashi
4,574,736 A * 3/1986 Tanaka et al. ........... 119/14.08

FOREIGN PATENT DOCUMENTS

| EP | 137367 | 11/1989 |
|---|---|---|
| EP | 397274 | 11/1990 |
| GB | 2124877 | 2/1984 |
| WO | WO 8303305 | 9/1983 |
| WO | WO 9522888 | 8/1995 |
| WO | 97/40374 | * 10/1997 |

* cited by examiner

Primary Examiner—Lyle A. Alexander
(74) Attorney, Agent, or Firm—Hovey Williams LLP

(57) ABSTRACT

A device for the measurement of an electrical parameter in the milk during the milking of an animal comprises a transportation member (1), arranged to transport the milk from a teat of said animal to a milk collecting member of a milking machine and forming a passage for the milk to be transported, and at least two electrodes (14–17) provided to be in contact with the milk flowing through the passage, and connected to an evaluation unit (18). The transportation member (1) comprises a wall member (5) provided in the passage and forming a groove (10) being open towards the passage, said electrodes (14–17) being provided on the wall member (5) in the groove (10). The wall member (5) is provided to receive a part of the milk flowing through the passage, said groove (10) being shaped in such a manner that at least a part of said received part quantity of the milk flows through the groove while contacting said electrodes (14–17).

19 Claims, 3 Drawing Sheets

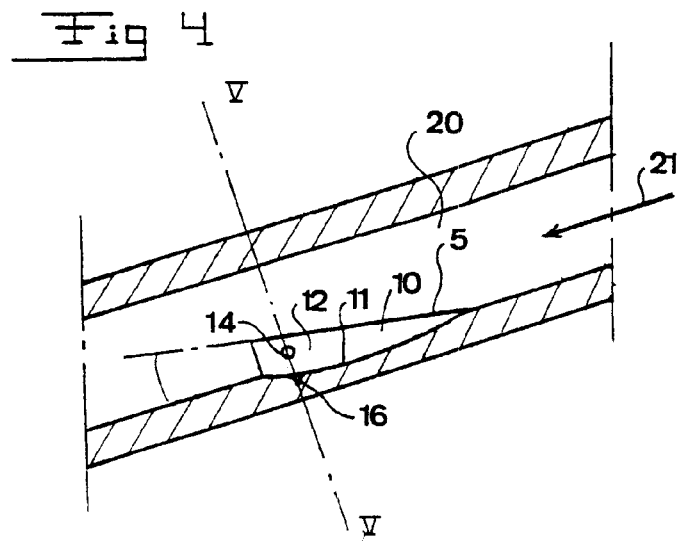
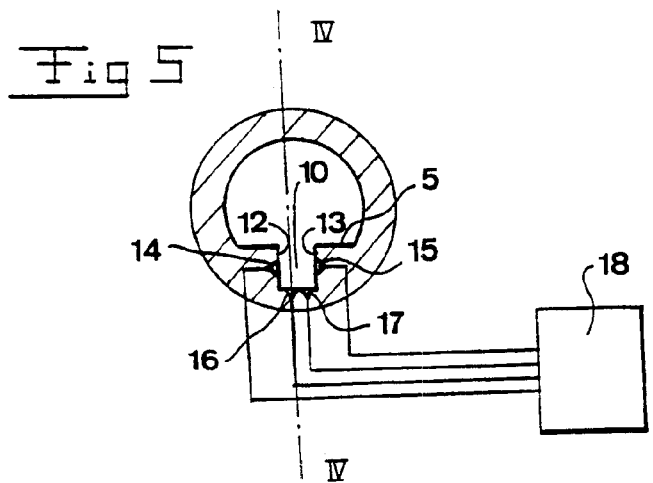
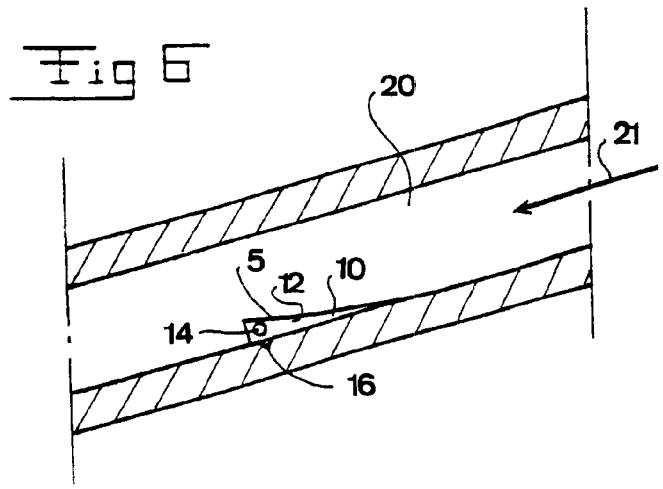

DEVICE FOR MEASURING AN ELECTRICAL PARAMETER IN THE MILK

BACKGROUND OF THE INVENTION

1. Field of the Invention

The present invention refers to a device for measuring an electrical parameter in the milk during the milking of an animal, comprising a transportation member, arranged to transport the milk from a teat of said animal to a milk collecting member of a milking machine and forming a passage for the milk to be transported, and at least two electrodes provided to be in contact with the milk flowing through the passage and connected to an evaluation unit.

2. Description of the Prior Art

It is known that the electrical conductivity of the milk is changed when the milk is infected because of mastitis or milk fever, for instance. In particular, the number of ions increases in these cases, resulting in an increase of the conductivity of the milk. By measuring the conductivity of the milk, it is thus possible to determine whether the milk is infected. An acute inflammation of an udder gives a relatively great change of the conductivity of the milk and is thus relatively easily detected by means of such a measurement. Theoretically, it is however a precondition that such a measurement of the conductivity is performed on a known volume and in practice this means that in order to obtain comparable conductivity values a certain quantity of milk has to be located between the measurement electrodes. If this quantity is not determined in a secure manner or is not equal at each milking occasion, merely a value of the conductance of the actual unknown milk quantity is obtained. In particular, in connection with latent inflammations of the udder, it is important that the measurement is performed on a certain quantity of milk since such a latent inflammation merely results in a small change of the conductivity of the milk.

EP-A-397 274 discloses a mastitis detector having electrodes for measuring the conductivity of the milk from a teat. The detector is provided in a milk conduit and comprises a cup shaped chamber which is open upwardly against the direction of the milk flow. The electrodes are provided in the bottom surface of the chamber. When the milk is flowing through the milk conduit a quantity thereof will be collected in the chamber and be in contact with the electrodes. Thereby, a measurement of the conductivity of the milk may be performed. However, the detector disclosed does not guarantee a flow through the chamber but at least a part of the collected milk quantity present in the chamber remains therein irrespective of how much milk is flowing through the milk conduit. This means that also when the milk flow has ceased the detector will provide a conductivity value for the milk which still may be present in the chamber.

GB-A-2 124 877 discloses a device for indicating a milk flow through a milk conduit of a milking machine. The milk conduit is provided between a claw and a collecting member of the milking machine. The milk conduit comprises two electrodes provided one after the other in the direction of the milk flow and each consisting of an open cylinder abutting the inner wall of the milk conduit. A voltage is applied to the electrodes and thus the variations in the conductance of the milk flowing through the milk conduit is measured. The result of these measurements are utilized for interrupting the milking when the mean value of said measurements falls below a certain value. However, by means of the device disclosed it is not possible to know how much milk there is between the two electrodes and therefore no reliable value of the conductivity of the milk may be obtained.

EP-B-137 367 discloses a milking device comprising measurement equipment for detecting the milk flow from an individual teat. The value detected may be utilized for determining when the milking from this teat is to be interrupted. The measurement equipment comprises two electrodes for each milk flow to be detected. According to a first embodiment, a milk conduit for a milk flow comprises a main passage and a secondary passage in which two electrodes are provided. At the end of the secondary passage there is a small hole permitting the milk to flow from the secondary passage back into the main passage. In such a manner a flow through the secondary passage is obtained. However, the small hole is very sensitive for dirt particles or fat agglomerations, which may be present in the milk and which tend to stop up the small hole. In such a manner the flow through the secondary passage is interrupted and no proper conductivity value for the milk is obtained. According to another very simple embodiment, the milk conduit comprises a throttling, and upstream of the throttling two electrodes. By this simple device it is merely possible to determine whether milk has been collected in the area above the throttling. It is to be noted that the throttling of course has to be provided in such a manner that it permits a relatively large milk flow therethrough. According to a third embodiment, the milk is conducted from each teatcup to a claw having a main passage. In addition, for each teatcup a secondary passage is provided in the claw in such a manner that a certain quantity of the milk from a teatcup will be conducted into a respective secondary passage. The secondary passage comprises two electrodes for measuring the conductivity of the milk being present in the secondary passage. In the same way as in the first embodiment, there is a small hole at the end of the secondary passage connecting the secondary passage to the main passage. In such a manner, a flow through the secondary passage is ensured. Also in this case the risk of stopping up the hole is significant.

U.S. Pat. No. 4,325,028 discloses a device for measuring the conductivity of the milk from each individual teat in a milk conduit between the teatcup and the claw. The measurement equipment comprises a receiving device, provided in each such milk conduit and having electrodes located therein, and an electronic evaluation device. The construction of the receiving devices are not described more closely. The aim of the device disclosed is to enable the determination whether the conductivity value of the milk from an individual teat is abnormal and thus whether any udder part is inflamed.

WO 83/03305 discloses an electrical conductivity device for detecting mastitis in the milk from a cow by measuring the conductivity of the milk. The device is intended in the first place for manual use although it is mentioned that it may be provided near a claw of a milking machine. The device is adapted to collect a minor secondary milk flow of the main milk flow and conduct this secondary milk flow through a testing passage in the form of a flexible tubing comprising two electrodes. The flexible tubing is relatively thin and there is a risk that dirt particles or fat agglomerations may stop up the milk flow therethrough.

WO 95/22888 discloses a claw for a milking machine having means for measuring the complex impedance, such as the electrical conductance and/or the capacitance, of the milk in order to detect mastitis. The claw comprises four inlet members and four chambers provided beneath a respective inlet member for collecting a part of the milk flowing through the inlet member into the claw. In the bottom wall of the chamber there is a small opening permitting the milk collected therein to slowly drain away. Also this known device provides a risk that dirt particles and fat agglomerations stop up the milk flow through the small opening.

SUMMARY OF THE INVENTION

The object of the present invention is to remedy the problems mentioned above and provide an improved device for measuring an electrical parameter of the milk. In particular, the invention aims at a device permitting the measurement of small milk flows and simultaneously ensuring a continuous milk flow through the measurement location.

This object is obtained by the device initially defined and characterized in that the transportation member comprises a wall member provided in the passage and forming a groove being open towards the passage, said electrodes being provided on the wall member in the groove, and that the wall member is provided to receive a part of the milk flowing through the passage, said groove being shaped in such a manner that at least a part of said received part of the milk flows through the groove while contacting said electrodes. By such a construction at least a part of the quantity of milk received by the wall member may be distributed in a continuous flow through the groove in such a manner that the latter always will be essentially filled with milk and thus the quantity of milk present between the electrodes is essentially determined. When the grooves are filled with milk it is thus possible to obtain a maximum value of a current flowing between the electrodes. This maximum value may be utilized for determining a comparable value of an electrical parameter, such as the conductance, the impedance, conductivity or resistivity, of the milk. The measurement device according to the invention may thus be utilized for detecting very small changes of the conductivity of the milk. Thereby, a possible state of illness of the animal may be detected at an early stage. By configuring the dimension of the groove in a proper manner, it will also, in the case of relatively small milk flows, be filled with milk and in such a way it is possible also in these cases to obtain such a maximum value. If the conductivity value obtained does not reach the maximum value there is an indication that the milk flow is very small and that the milking process may be interrupted. By comparing the maximum values obtained for the conductivity at different milking occasions one may determine whether the animal is suffering from any decease, for instance mastitis. By such an open groove, the risk of dirt, fat agglomerations or particles of any kind getting clogged in the groove, thereby obstructing the flow through the groove, is substantially reduced. Such a groove is also advantageous from a cleaning point of view as such an open groove is accessible for the injection of cleaning liquid, for instance. Preferably, the groove is shaped in such a manner, with regard to its width and inclination when the transportation member is in an operating position, that the milk flow through the groove is essentially secured. It means that in the case of a small milk flow from the actual teat, a relatively large part of the milk will flow through the groove, in an extreme case essentially all milk, and at a large milk flow a relatively small part of the milk will flow through the groove. In such a manner the measurement will always be performed with respect to the actual milk flow, i.e. the measurement may not be deteriorated by milk remaining in the groove. This also means that by the measurement device according to the invention it is possible to determine in a very reliable manner whether an individual teat produces any milk since if that is the case no milk will remain in the groove.

According to an embodiment of the invention, the wall member comprises a concave surface arranged to collect said part of the milk, the groove extending through said concave surface. Such a concavely shaped wall member will be able to keep said part of the milk and during a certain period of time continuously discharge said part through the groove.

According to an advantageous application of the invention, the transportation member comprises a claw through which the passage extends and in which the wall member is provided. Thereby, the claw may comprise an inlet arranged to permit the supply of the milk to the claw from said teat and the wall member may be provided beneath the inlet when the claw is in an operating position. Furthermore, the concave surface of the wall member faces the inlet. Consequently, the space being present in a claw may advantageously be utilized for the measurement equipment according to the invention. It is to be noted, in particular, that such a claw permits an individual measurement of the electrical parameter of the milk from each of the teats of the animal.

According to a further embodiment of the invention, the groove extends essentially in the flow direction of the milk flowing through the passage. Such a shape also facilitates a continuous flow of milk through the groove. The groove will have no retarding influence on the milk flow through the passage.

According to a further embodiment of the invention, the electrical parameter comprises the conductivity of the milk. Thereby, the groove may have such a depth that a distinguishable maximum value is obtained during the measurement of the conductivity of the milk.

According to a further embodiment of the invention, the groove comprises a longitudinal bottom surface and two longitudinal side surfaces. Preferably, the width of the groove, i.e. the distance between the longitudinal side surfaces, is about 1–6 mm, preferably 2–5 mm. Furthermore, the groove may in the area of the electrodes have a height of about 5–20 mm, preferably 10–15 mm. Preferably, the electrodes are provided essentially opposite to each other on a respective side surface. Furthermore, they may be provided about 0–10 mm, preferably 0–5 mm, above the bottom surface.

According to a further embodiment of the invention, the device comprises four electrodes provided in the groove. Thereby, two of the electrodes may be provided essentially opposite to each other on a respective side surface and two of the electrodes may be provided on the bottom surface. Furthermore, the evaluation unit may be arranged to perform a four-pole measurement by means of the electrodes in such a manner that a voltage is provided between the electrodes provided on the side surfaces, and that the current, required for providing a voltage drop of a predetermined level between the two electrodes provided on the bottom surface, is measured.

BRIEF DESCRIPTION OF THE DRAWINGS

The present invention shall now be explained more closely by means of different embodiments, disclosed by way of example, and with reference to the drawings attached hereto.

FIG. 4 discloses a sectional view through a milk conduit having a wall member according to another embodiment of the invention.

FIG. 5 discloses a sectional view along the line V—V in FIG. 4.

FIG. 6 discloses a sectional view similar to the one in FIG. 4 and having a modified wall member.

DETAILED DESCRIPTION OF DIFFERENT EMBODIMENTS

Figure 1:
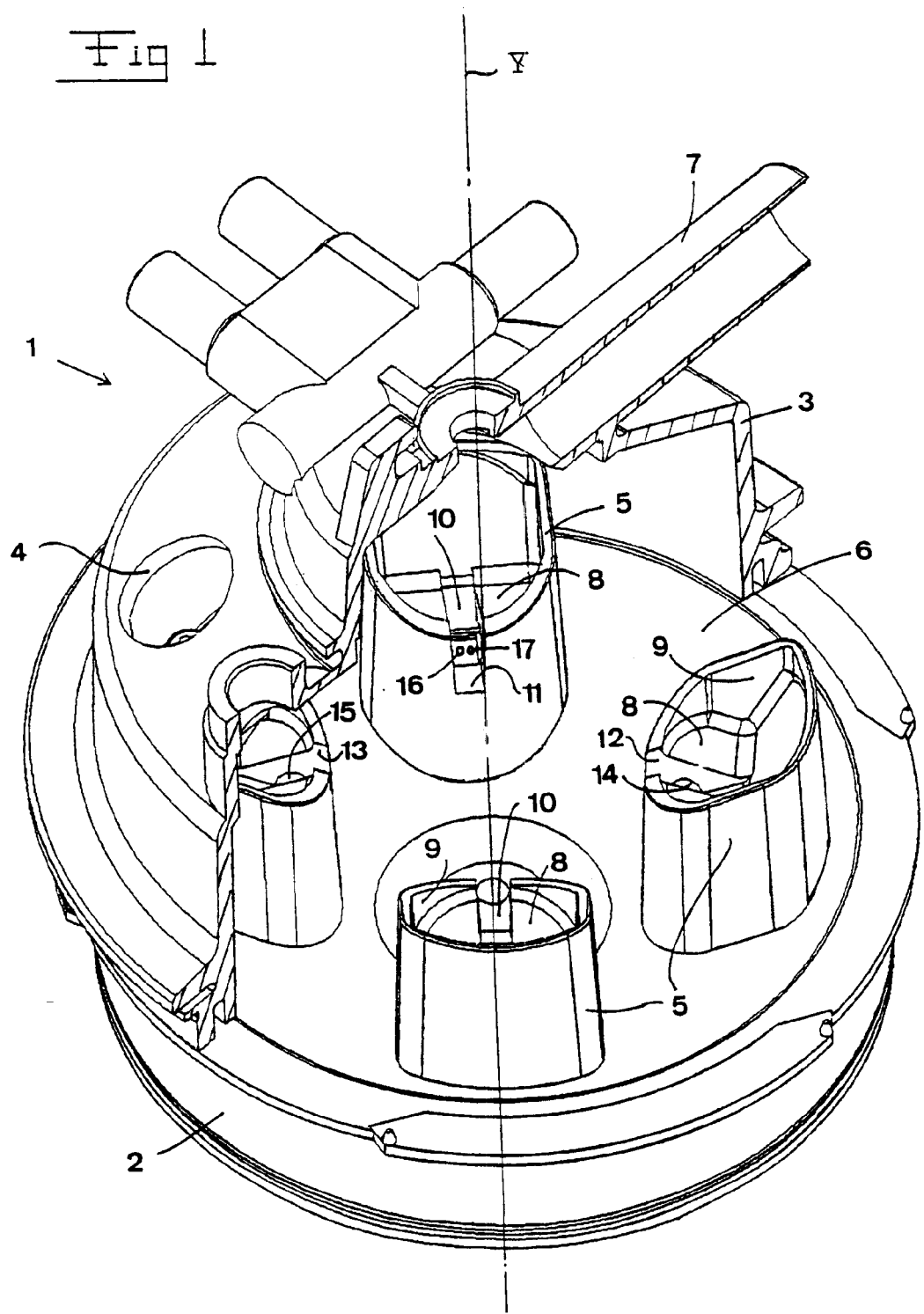
FIG. 1 discloses a view of a partly sectioned claw having four wall members according to an embodiment of the invention for receiving milk from four respective teats.
Figure 2:
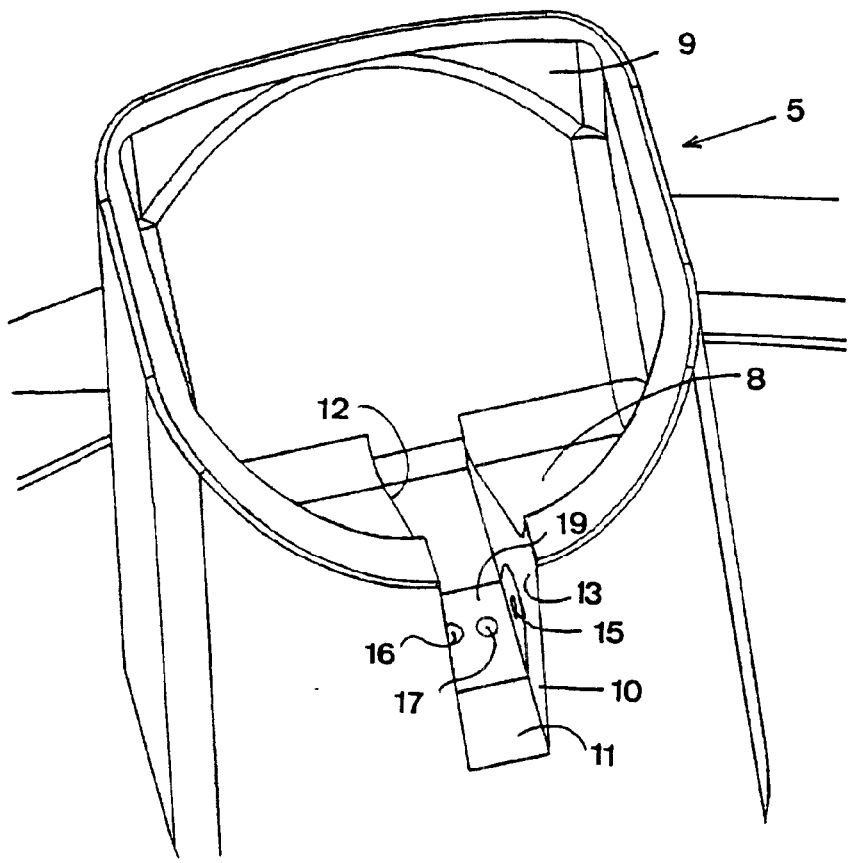
FIG. 2 discloses an enlarged view of a wall member according to FIG. 1.
Figure 3:
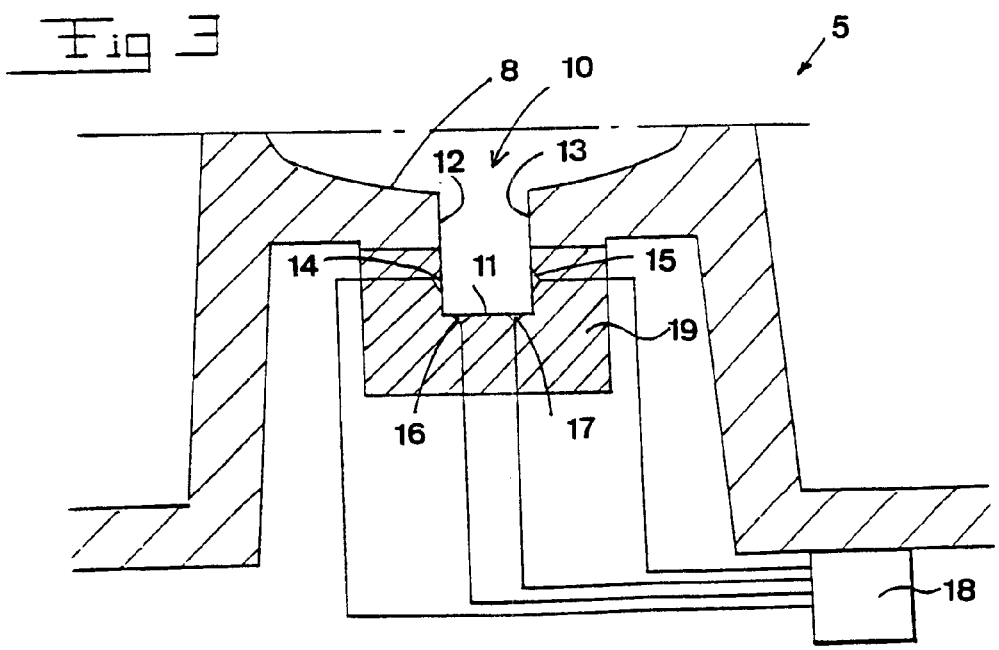
FIG. 3 discloses a sectional view through a wall member according to FIG. 2.

With reference to FIGS. 1–3, a first embodiment of the measuring device according to the invention is disclosed. FIG. 1 discloses a claw 1 having a lower portion 2 and an upper portion 3, merely the half thereof being disclosed. Through the upper portion 3 and the lower portion 2 a center axis Y extends, which is vertical when the claw 1 is in an operating position. The upper portion 3 comprises four inlet members 4, merely one thereof being disclosed. Each inlet member 4 is arranged to receive a short milk conduit which at its other end is connected to a teatcup (not disclosed). During milking, the milk from the four teatcups will thus be introduced into the claw 1 via a respective milk conduit and a respective inlet member 4. Beneath each inlet member 4 there is a wall member 5 configured as a receiving cup and arranged to receive at least a part of the milk being introduced through the inlet member 4. The four receiving cups 5 are provided on a concave plate 6 sloping downwardly to a lowest area in the center of the plate 6, where it is intersected by the center axis Y. The plate 6 may form a part of the lower part 2 of the claw 1 or an element provided in the lower part 2. The milk flowing into the claw 1 is thereafter flowing downwards to the lowest area of the plate 6 and from there transported upwardly through a vertical suction pipe (not disclosed) centrally positioned and out through an outlet nipple 7. From the outlet nipple 7, the milk is transported via a milk conduit to a collecting member of a milking machine (not disclosed). Each receiving cup 5 comprises an upper concave surface 8 for receiving said part of milk. The concave surface 8 is configured in such a manner that it slopes downwardly in essentially each point to a lowest point of the surface 8. Around the surface 8 a wall 9 extends, which is essentially vertical or slopes somewhat downwardly and inwardly to the center of the receiving cup 5. The wall 9 extends to a higher level at the end of the receiving cup 5 facing away from the center axis Y and is at a lowest level at the end of the receiving cup 5 facing the center axis Y. Through the surface 8, and in particular its lowest point, and the wall 9, a groove 10 extends in the direction towards the center axis Y of the claw. Thus, the milk hitting the concave surface 8 and received in the receiving cup 5 will flow out through the groove 10. In the example disclosed, the receiving cup 5 is provided in such a manner that the groove 10 is directed inwardly towards the center axis Y. Since the milk from the inlet member 4 flows downwardly somewhat obliquely inwardly towards the center, the groove 10 extends in essentially the direction of the whole milk flow. However, it is to be noted that the receiving cups 5 may be turned in such a manner that the groove 10 is directed in an arbitrary direction, for example radially outwardly from the center axis Y.

Each groove comprises a bottom surface 11 and two side surfaces 12 and 13, see also FIGS. 2 and 3. The bottom surface 11 of the groove 10 slopes downwardly with respect to the vertical axis Y. It is to be noted that the groove may have another cross-section shape than the one disclosed. For example, the corner between the side walls and the bottom surface may be rounded, which means that no clearly defined borderline exists therebetween. It may also be imagined that the groove has a semicircular or semi-oval cross-section.

In the groove 10, there are four electrodes 14–17. Two of the electrodes 14 and 15 are provided on a respective side surface 12 and 13 and the two other electrodes 16 and 17 are provided at the bottom surface 11. All the electrodes 14–17 lie in a plane being perpendicular to the flow direction of the milk through the groove 10. The four electrodes 14–17 are connected to an evaluation unit 18 which is schematically disclosed in FIG. 3 and which for example may be attached to the lower part 2 or to the lower side of the plate 6. By the electrode arrangement disclosed, it is possible to perform a so called four-pole measurement, i.e. a relatively high voltage is provided between the electrodes 14 and 15 provided on the side surfaces 12 and 13, and thereby the current, required for providing a voltage drop of a predetermined level between the two electrodes 16 and 17 provided on the bottom surface, is measured. It is to be noted that the measuring device disclosed also may be used for a two-pole measurement using merely two electrodes. Thereby, one electrode is preferably provided on a respective side surface 12 and 13. As is disclosed in FIGS. 2 and 3 the electrodes 14–17 may be attached to a holding member 19 being introduced from below into a recess in the receiving cup 5.

The groove 10 which is open upwardly is to be configured in such a manner, with respect to its width and inclination, that the milk flow therethrough is essentially secured. The groove 10 also has to have such dimensions that it in case of a relatively small milk flow from the actual teat will be essentially filled with milk. This is essential for obtaining a comparable conductivity value. Thereby, the distance between the longitudinal side surfaces 12 and 13 may be about 1–6 mm, preferably 2–5 mm, for example about 4 mm. Furthermore, the height of the groove 10 in the plane in which the electrodes 14–17 are located may be about 5–20 mm, preferably 10–15 mm. The electrodes 14 and 15 provided on the side surfaces 12 and 13 may be located about 0–10 mm, preferably 0–5 mm above the bottom surface 11.

With reference to FIGS. 4–6, some alternative embodiments of the measuring device according to the invention are now to be explained more closely. Thereby, it is to be noted that for elements having a corresponding function the same reference signs have been used as in the first embodiment. FIG. 4 discloses a transportation member 20 which may be a pipe portion of a milk conduit from a teatcup. Such a pipe portion 20 is especially preferable when no claw is used. It is to be noted that the pipe portion 20, as it is located in an operating position, slopes in relation to a horizontal plane in such a manner that the flow of the milk in the direction of the arrow 21 is secured. The pipe portion 20 comprises a wall member 5 extending upwardly from the lower inner surface of the pipe portion 20 by an angle v. As is disclosed in FIG. 5, a groove 10 is provided in the wall member 5. Four electrodes 14–17 are provided in a corresponding manner as in the first embodiment and the electrodes 14–17 are connected to an evaluation unit 18 schematically disclosed. Advantageously, the groove 10 has, also in this embodiment, the same dimensions as defined for the groove 10 according to the first embodiment. The depth of the groove 10 may be determined by either the height of the wall member 5 above the inner surface of the pipe portion 20 or by the fact that the bottom 11 of the groove is concavely shaped, as is disclosed in FIGS. 4 and 5, and thus extends in the wall of the pipe portion 20. In an extreme case the inclination angle v may be 0°, i.e. the wall member 5 is formed by the inner wall of the pipe portion 20 and the groove 10 is formed by a groove 10 made in the wall of the pipe portion 20. As is disclosed in FIG. 6, the wall member 5 may be concave in a longitudinal section through the pipe portion 20. In FIG. 5 is disclosed that the wall member 5 is plane in a cross-section of the pipe portion 20 but it is to be noted that the wall member 5 also in a cross-section may have a concave shape in order to secure that a greater part of the milk received by the wall member 5 will flow downwardly in the groove 10.

The present invention is not limited to the embodiments disclosed above but may be varied and modified within the scope of the following claims.

What is claimed is:

1. A device for measuring an electrical parameter in the milk during the milking of an animal and conveying a value corresponding to the electrical parameter to an evaluation unit, said device comprising:

a transportation member arranged to transport the milk from a teat of said animal to a milk collecting member of a milking machine and forming a passage for the milk to be transported; and at least two electrodes mounted on said transportation member and positioned to be in contact with the milk flowing through the passage and connected to the evaluation unit, wherein the transportation member comprises a wall member provided in the passage and forming a groove extending substantially in the flow direction of the milk flowing through the passage wherein the groove is open towards the passage along the entire length of the groove, said electrodes being provided on the wall in the groove, the groove being provided to receive a part of the milk flowing through the passage, and said groove being shaped in such a manner that at least a part of said received part of the milk flows through the groove while contacting said electrodes.

2. A device according to claim 1, wherein said groove is shaped in such a manner, with regard to its width and inclination when the transportation member is in an operating position, that a milk flow therethrough is essentially secured.

3. A device according to claim 1, wherein the wall member comprises a concave surface arranged to receive said part of the milk and that the groove extends through said concave surface.

4. A device according to claim 3, wherein the concave surface of the wall member faces the inlet.

5. A device according to claim 1, wherein the transportation member comprises a claw through which the passage extends and in which the wall member is provided.

6. A device according to claim 5, wherein the claw comprises an inlet arranged to permit the supply of the milk to the claw from said teat and that the wall member is provided beneath the inlet when the claw is in an operating position.

7. A device according to claim 1, wherein the electrical parameter comprises the conductivity of the milk.

8. A device according to claim 7, wherein the depth of the groove is such that a distinguishable maximum value is obtained during the measurement of the conductivity of the milk.

9. A device according to claim 1, wherein the groove comprises a longitudinal bottom surface and two longitudinal side surfaces.

10. A device according to claim 9, wherein the groove has a width defined as the distance between the longitudinal side surfaces, said width being about 1–6 mm.

11. A device according to claim 10, wherein the width of the groove is about 2–5 mm.

12. A device according to claim 9 wherein the groove in the area of the electrodes has a height of about 5–20 mm.

13. A device according to claim 12, wherein the groove in the area of the electrodes has a height of about 10–15 mm.

14. A device according to claim 9, wherein the electrodes are provided essentially opposite to each other on a respective side surface.

15. A device according to claim 14, wherein the electrodes are positioned about 0–10 mm above the bottom surface.

16. A device according to claim 15, wherein the electrodes are positioned about 0–5 mm above the bottom surface.

17. A device according to claim 9, wherein are mounted on said transportation member and positioned and configured to contact the milk flowing in the groove.

18. A device according to claim 17, wherein two of the electrodes are provided essentially opposite to each other on a respective side surface and that two of the electrodes are provided on the bottom surface.

19. A device according to claim 17, wherein the evaluation unit is arranged to perform a four-pole measurement by means of the electrodes in such a manner that a voltage is provided between the electrodes provided on the side surfaces, and that the current, required for providing a voltage drop of a predetermined level between the two electrodes provided on the bottom surface, is measured.

* * * * *